(12) United States Patent
Green

(10) Patent No.: US 8,343,130 B2
(45) Date of Patent: Jan. 1, 2013

(54) NEEDLELESS INJECTOR

(75) Inventor: Terry Green, Norfolk (GB)

(73) Assignee: Zogenix, Inc., Emeryville, CA (US)

( * ) Notice: Subject to any disclaimer, the term of this patent is extended or adjusted under 35 U.S.C. 154(b) by 0 days.

(21) Appl. No.: 13/088,140

(22) Filed: Apr. 15, 2011

(65) Prior Publication Data

US 2011/0257624 A1    Oct. 20, 2011

Related U.S. Application Data

(63) Continuation of application No. 12/021,052, filed on Jan. 28, 2008, now abandoned, which is a continuation of application No. 10/493,368, filed as application No. PCT/GB02/04703 on Oct. 18, 2002, now abandoned.

(30) Foreign Application Priority Data

Oct. 24, 2001 (GB) .................................. 0125506.6

(51) Int. Cl.
*A61M 5/30* (2006.01)

(52) U.S. Cl. .......................................... 604/500; 604/68

(58) Field of Classification Search ............... 604/68, 604/500
See application file for complete search history.

(56) References Cited

U.S. PATENT DOCUMENTS

| | | | |
|---|---|---|---|
| 2,322,244 A | 6/1943 | Lockhart | |
| 2,704,543 A * | 3/1955 | Scherer | 604/68 |
| 2,737,946 A | 3/1956 | Hein, Jr. | |
| 2,902,994 A * | 9/1959 | Scherer | 604/68 |
| 3,507,276 A | 4/1970 | Burgess | |
| 4,089,334 A * | 5/1978 | Schwebel et al. | 604/69 |
| 4,623,332 A * | 11/1986 | Lindmayer et al. | 604/68 |
| 4,722,728 A | 2/1988 | Dixon | |
| 4,913,699 A * | 4/1990 | Parsons | 604/68 |
| 5,062,830 A * | 11/1991 | Dunlap | 604/68 |
| 5,520,639 A | 5/1996 | Peterson et al. | |
| 5,599,302 A | 2/1997 | Lilley et al. | |
| 5,704,911 A | 1/1998 | Parsons | |
| 5,722,953 A | 3/1998 | Schiff et al. | |
| 5,769,138 A * | 6/1998 | Sadowski et al. | 141/329 |
| 5,782,802 A | 7/1998 | Landau | |
| 5,800,388 A | 9/1998 | Schiff et al. | |
| 5,846,233 A | 12/1998 | Lilley et al. | |
| 5,875,976 A | 3/1999 | Nelson et al. | |
| 5,891,085 A | 4/1999 | Lilley et al. | |
| 5,891,086 A | 4/1999 | Weston | |
| 5,911,703 A * | 6/1999 | Slate et al. | 604/68 |
| 6,013,050 A | 1/2000 | Bellhouse et al. | |
| 6,135,979 A | 10/2000 | Weston | |

(Continued)

FOREIGN PATENT DOCUMENTS

EP    0276158 A    7/1988

(Continued)

*Primary Examiner* — Kevin C Sirmons
*Assistant Examiner* — Michael J Anderson
(74) *Attorney, Agent, or Firm* — Karl Bozicevic; Bozicevic, Field & Francis LLP

(57) ABSTRACT

A needleless injector has a syringe body having an opening at one end, a piston housed within the syringe body for urging a liquid within the syringe body through the opening and a ram for driving the piston. A shock absorbing component is provided for reducing an initial transfer of force from the ram to the piston. The initial rate of pressure increase on the liquid is reduced, thereby controlling the rate of collapse of gas bubbles in the liquid.

27 Claims, 5 Drawing Sheets

U.S. PATENT DOCUMENTS

| | | | |
|---|---|---|---|
| 6,309,371 B1 * | 10/2001 | Deboer et al. | 604/68 |
| 6,391,003 B1 | 5/2002 | Lesch | |
| 6,613,010 B2 | 9/2003 | Castellano | |
| 6,673,038 B2 | 1/2004 | Weston | |
| 6,685,669 B2 | 2/2004 | Bellhouse et al. | |
| 6,913,593 B1 | 7/2005 | Alexandre et al. | |
| 7,018,356 B2 | 3/2006 | Wise et al. | |
| 7,056,300 B2 | 6/2006 | Alexandre et al. | |
| 7,074,210 B2 * | 7/2006 | Leon et al. | 604/192 |
| 7,160,265 B2 * | 1/2007 | Lell | 604/69 |
| 2003/0050596 A1 | 3/2003 | Alexandre et al. | |
| 2005/0154346 A1 | 7/2005 | Green | |

FOREIGN PATENT DOCUMENTS

| | | |
|---|---|---|
| JP | 2000-14780 | 1/2000 |
| WO | WO 01/64269 | 9/2001 |

* cited by examiner

NEEDLELESS INJECTOR

CROSS REFERENCES

This application is a continuation of U.S. patent application Ser. No. 12/021,052, filed Jan. 28, 2008 (now abandoned), which application is a continuation of U.S. patent application Ser. No. 10/493,368 filed Mar. 7, 2005 (now abandoned), which application is a 371 National Phase Filing of PCT/GB02/04703 filed Oct. 18, 2002, which was published on May 1, 2003 as publication number WO 03/035149, which application claims the benefit of priority to United Kingdom patent application serial no. 0125506.6 filed Oct. 24, 2001 all of which applications are incorporated herein in their entirety.

BACKGROUND TO THE INVENTION

Needlefree injectors are used as an alternative to needle-type hypodermic injectors for injecting liquid drugs through the epidermis and into the underlying tissues. The usual form of construction for such a device is a syringe having a small discharge orifice which is placed in contact with the skin, and through which the drug is injected at a sufficiently high speed to penetrate the skin of the patient. The energy required to pressurise the drug may be derived from a compressed coil spring, compressed gas, explosive charge or some other form of stored energy.

There are a number of different ways in which the energy may be converted from the stored form into pressure in the liquid. These may include rupturing a seal, so allowing gas to escape from a canister and causing pressure to build up behind a piston which pressurises the gas. Alternatively, a gas may cause a ram to accelerate across a gap, prior to impacting on the back of a piston.

Whichever method is used to pressurise the fluid, it is important that the peak pressure in the fluid is achieved quickly enough to enable the initial 'pulse' of fluid to have a sufficiently high pressure to penetrate the skin. The remainder of the fluid may be delivered at a similar pressure, or a substantially lower pressure, depending on the configuration of the device. Some needle free devices are designed to be filled by the user, whilst others are prefilled, either by the drug manufacturer or by a third party. In either case, it is important that the contents of the drug capsule are predominantly free from bubbles, especially in the nozzle area.

SUMMARY OF THE INVENTION

The invention is based on the recognition that a very rapid rise in pressure in the drug can give rise to a rapid collapse of the bubbles in the drug. This bubble collapse, if it occurs quickly enough, can cause shock waves within the capsule, which can give rise to extremely high localised stresses. These stresses can sometimes cause the capsule to fail during this initial pressure peak, which is likely to result in an incomplete injection.

The inventors have recognised that it would therefore be beneficial to ensure that the collapse of any bubble that may be present in the capsule (either because of the filling process, or because of arty gas that may come out of the drug solution due to changes in temperature, pressure etc.) is in a slow controlled manner. It has been found that, depending on the material and geometry of the capsule, bubbles greater than around 0.5-1 µl can increase the probability of the capsule breaking.

It has also been found that the key factor giving rise to these shock waves is the initial rate of pressure increase. The peak pressure in the fluid may be around 200-400 Bars, and yet by slowing the rate of pressure increase from atmospheric pressure to around 20 Bars still has a dramatic effect on reducing the shock wave generation, even if the remainder of the pressure increase occurs at the same rate as previously.

The invention provides a method of preventing a collapsing bubble from causing a needle free injector capsule to break, and comprises the step of causing the bubble to collapse in a slower, controlled manner immediately prior to the normal injection cycle, without changing the peak value or the shape of the remainder of the pressure profile. The invention also provides an apparatus for this purpose.

According to a first aspect of the invention, there is provided a needleless injector comprising:
  a syringe body having an opening at one end;
  a piston housed within the syringe body for urging a liquid within the syringe body through the opening;
  a ram for driving the piston;
  means for applying a force to the ram; and
  shock absorbing means for reducing an initial transfer of force from the ram to the piston.

This apparatus provides reduction of the initial force applied to the ram, so that the initial rate of pressure increase on the liquid is reduced, thereby controlling the rate of collapse of gas bubbles in the liquid.

The shock absorbing component may be provided in the gap across which the ram is accelerated prior to impact with the piston.

The shock absorber may comprise a cylinder, in which the ram (or a portion thereof) is slidably received. This cylinder can be closed at one end, and the closed end lies adjacent the piston. The ram is then received adjacent the open end of the cylinder before application of force to the ram. In this way, shock absorbing is achieved by driving the ram into a cylinder. Preferably, the ram is also slidably received in the cylinder with a fluid tight fit, so that as the ram progresses into the cylinder, a volume of gas trapped in the cylinder is compressed, thereby providing a gradually increasing force on the piston.

In another arrangement, the cylinder can be open at both ends. The internal opening of the cylinder may have a constant internal diameter, or else the internal opening of the cylinder may have at least two internal diameters, a first internal diameter at an end of the cylinder for cooperation with the ram, and a second smaller internal diameter.

This provides a step in the internal profile, which provides a local pressure peak which results in a low initial pressure for ensuring bubble collapse. The internal opening of the cylinder can have three internal diameters, a third internal diameter at an end of the cylinder for cooperation with the piston, the third internal diameter being greater than the second internal diameter. The third internal diameter can be equal to or greater than the diameter of the ram, so that this section of the component does not increase the frictional resistance to the ram, but provides length over which the initial pressure continues to act before impact of the ram with the piston.

The cylinder may have a length of between 1 mm and 5 mm, and this short initial absorbing of the movement of the ram acts to reduce the applied force. The shock absorber may comprise a different compressible member.

The invention also provides a method of delivering liquid from a needleless injector syringe which comprises a piston housed within a syringe body and a ram for driving the piston thereby causing liquid to be driven out of the syringe, the method comprising:
  applying a force profile to the ram;

during a first stage of the delivery cycle, at least partially absorbing the force applied to the ram and applying the reduced force to the piston; and during a second stage of the delivery cycle, transferring substantially the full force applied to the ram to the piston.

This method provides a two-stage process, with damping in the first process only.

BRIEF DESCRIPTION OF THE DRAWINGS

An example of the invention will now be described in detail with reference to the accompanying drawings, in which.

DETAILED DESCRIPTION

Figure 1:
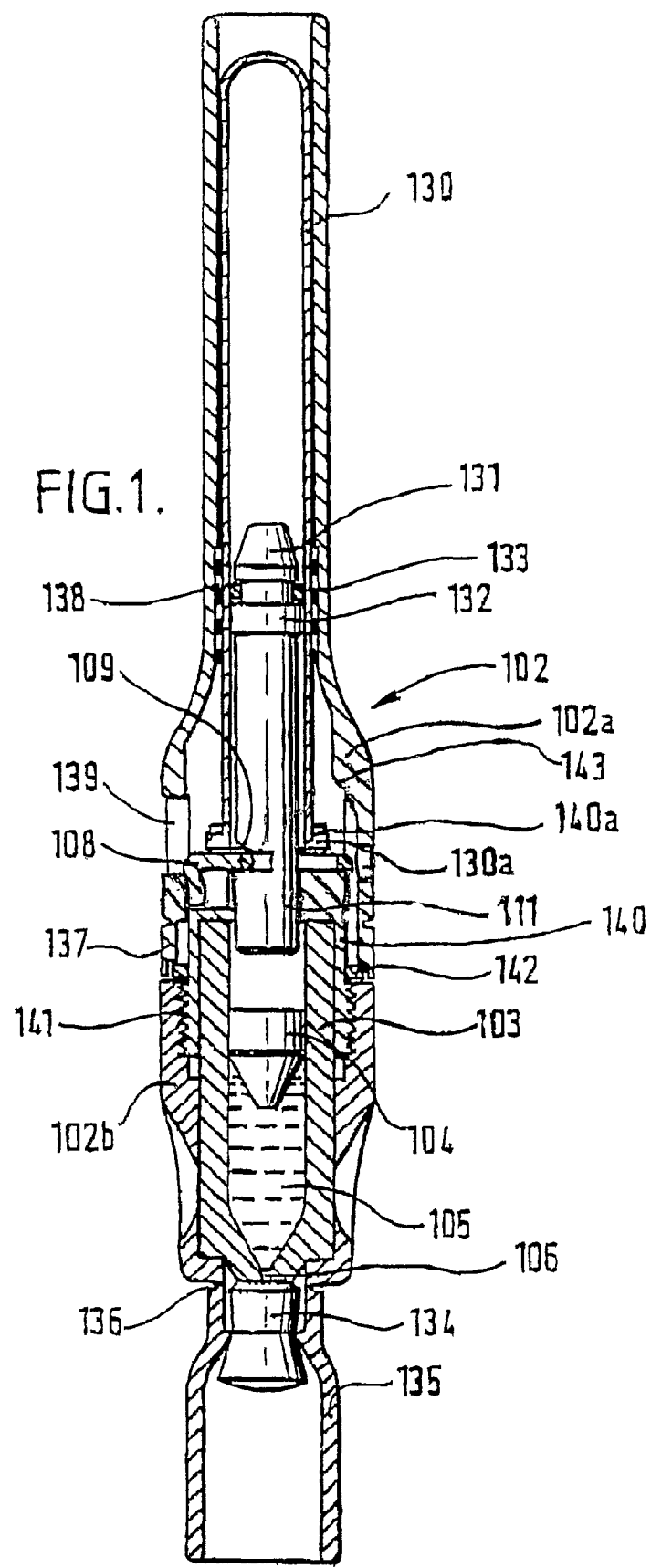
FIG. 1 shows a known needleless injector.

FIG. 1 shows a known needleless injector, comprising a syringe body in the form of a cartridge 103 having an opening 106 at one end. A piston 104 is housed within the cartridge 103 for urging a liquid 105 within the cartridge through the opening 106. A ram 111 is provided for driving the piston, and an arrangement is provided for applying a force to the ram 111.

The are numerous possible ways of applying force to the ram. In the example shown, the injection force is provided by a compressed gas spring. This is in the form of a cylinder 130 which is closed at its upper end and which contains gas, typically air, under a pressure which is typically in the range 5.5 MPa (800 psi) to 22 MPa (3000 psi). The cylinder houses the ram 111. The end of the ram 111 has a frustoconical portion 131 and a flange 132 between which is situated an O-ring seal 133. Prior to use, the ram 111 is held in the illustrated position by a latch 108 engaging in a groove in the ram, the upper surface of the groove forming a cam surface 109.

The lower end of the cylinder 130 has an outwardly directed flange 130a, which enables the cylinder to be held by crimping the flange 130a beneath an outwardly directed flange 140a at the upper end of a coupling 140. The sleeve 102 is formed of an upper sleeve portion 102a within which the cylinder is situated, and a lower sleeve portion 102b. The sleeve portion 102b is connected to the coupling by the interengaging screw threads 141 formed on the inner and outer walls of the sleeve portion 102b and coupling 140 respectively.

The ram arrangement, of the compressed gas cylinder 130 and the ram 111, are assembled to form a first component which is subsequently attached to the cartridge assembly.

The injector contains the medicament cartridge 103 in which the piston 104 is slidingly and sealingly located therein, in contact with medicament 105. As considered from the upper end of FIG. 1, the piston may comprise a cylindrical portion, a larger diameter cylindrical sealing portion, and a frusto-conical portion. The opening 106 is sealed by a resilient seal 134 which is held in place by a seal carrier 135. The seal carrier 135 is connected to the lower sleeve portion 102b by a frangible joint 136.

As a precaution against accidental firing, a tear-off band 137 is provided as the lower part of the upper sleeve portion 102a. The lower edge of the tear-off band 137 bears against a ring 142 which is bonded to the exterior surface of the coupling 140 or (not shown) formed integrally therewith. The function of the ring is to prevent downward movement of the sleeve portion 102a relative to the coupling 140, for so long as the tear-off band 137 is present. Accordingly, the ring 142 need not extend completely around the periphery of the coupling, and could be replaced by one or more separate elements.

An annular space 138 is formed in the inside wall of the sleeve 102, where the sleeve is adjacent the cylinder 130, and the space is filled with a damping grease (indicated diagrammatically by a succession of black bands), so that the grease is in intimate contact both with the sleeve 102 and the cylinder 130. It should be noted that although a defined annular space is convenient from the point of view of providing a particular location for the grease, it could be omitted and the grease simply smeared over all or part of the outside of cylinder 130 and/or inside of sleeve 102.

When the embodiment of FIG. 1 is to be operated, the user snaps off the seal carrier 135 at the frangible joint 136, which takes the seal 134 with it and exposes the orifice 106. The user then removes the tear-off band 137, and grasping the upper part of the sleeve 102 urges the orifice against the skin which is to be injected. This moves the upper sleeve portion 102a downwardly, with respect to the lower sleeve portion 102b. This brings aperture 139 in the wall of the Upper sleeve portion 102a into alignment with the latch 108, which is thus able to move sideways into the aperture under the influence of the force of the gas within the cylinder 130 acting on the latch via the cam surface 109 formed in the ram 111. The injector is thus caused to fire. As a precaution, in case the latch fails to move under the influence of the cam surface 109, an auxiliary cam surface 143 is provided on the inside of the sleeve portion 102a. The resulting recoil is damped by the damping grease.

As discussed above, gas bubbles within the liquid 105 must be avoided, because the rapid increase in pressure in the liquid after firing can result in any such bubbles affecting the injection performance.

Figure 2:
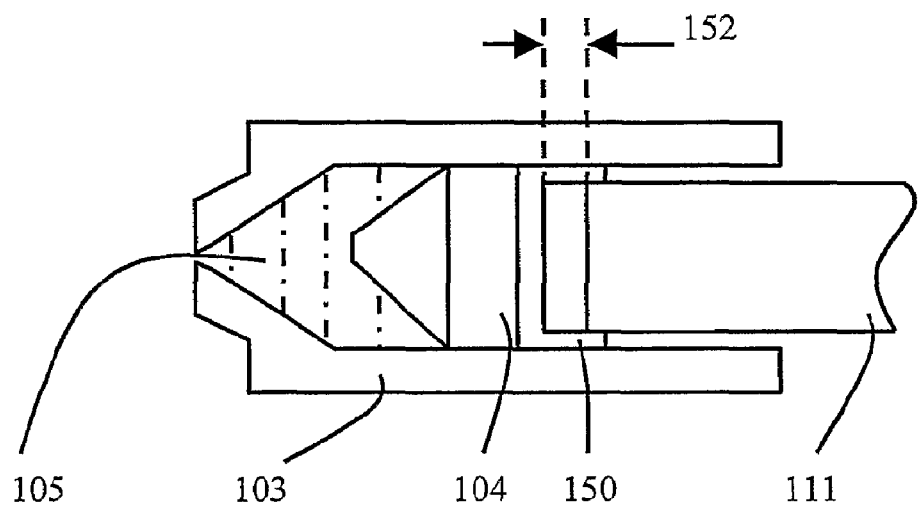
FIG. 2 shows a modification to the injector of FIG. 1 using a first example of shock absorbing component of the invention.

As shown in FIG. 2, the invention provides a shock absorbing component 150 between the ram and the piston for reducing an initial force applied to the ram. The component fills the gap across which the ram is accelerated.

In one embodiment of the invention shown in FIG. 2, a blind tube is used as the shock absorbing component 150, which is an interference fit with a portion of the ram 111 that accelerates towards the piston. The blind tube comprises a hollow cylinder which is closed at one end, the closed end lying adjacent the piston, and the ram is received adjacent the open end of the cylinder before application of force to the ram (as in FIG. 2).

The component 150 can be formed from PTFE, and is then machined to form the desired shape. It may be formed integrally with the piston 104. Alternatively, other high density and resilient materials may be used, such as high density polyurethane ("CHDPE"}, which can be moulded.

In the example shown, the cylinder 150 rests behind the piston 104 (or may be formed integrally with it as mentioned above), and is in contact with it. As the ram 111 accelerates, two phenomena occur. Firstly, friction between the ram 111 and the cylinder 150 causes a force to be applied to the piston 104. This force is very much smaller than the subsequent impact force between the ram 111 and the piston 104. Secondly, the interference fit between the portion of the ram 111 and the cylinder 150 causes a gas tight seal. Therefore, as the ram 111 moves down inside the cylinder 150, the pressure in the cylinder increases, resulting in a gradually increasing force to be applied to the piston 104 by the cylinder 150. As this force increases, the piston 104 is moved forward slightly, which causes any bubble to be compressed. Typically, in one embodiment of the invention, the ram accelerates across a gap 152 of 3 mm, in about 200 µs. This causes a substantially steady increase in pressure from 0 to around 1-5 Mpa over this time. This causes a gradual collapse of the bubble over this period, from its original size, to a tiny fraction (for example ½₀) of its size. Furthermore, if the bubble is in, or very close to, the opening of the cartridge 103, it is likely to be pushed out of the orifice.

The effect of this is that, when the ram 111 impacts on the blind (closed) end of the cylinder 150, which in turn is in contact with the back of the piston 104, there will be no bubble present in the capsule of a significant size. This means that, despite the extremely rapid rise in pressure caused by this impact, and necessary to penetrate the skin, there will not be high localised stresses and shock waves caused by the collapse of large bubbles. The gradual collapse of the bubble caused by the increase in pressure to around 1-5 MPa, means that any bubble previously smaller than 10 µl, will be below the critical size of 0.5 µl at the time when the ram impacts the piston.

In an alternative arrangement; the component 150 can be seated over the end of the ram 111, and thus form part of the ram arrangement. For example, the component can be placed over an end of the ram 111 which projects beyond an end face of the assembled ram arrangement. This end face can then act as a stop to limit the positioning of the component 150 over the ram 111. When the ram is released, the component 150 moves with the ram inside the cartridge 103 until it strikes the piston 104. Only then is the shock absorbing function of the component 150 used.

This design enables the component to be introduced as a modification which does not require any change to an existing ram arrangement or to the cartridge assembly design.

The shock absorbing component reduces the initial rate of pressure increase within the drug-containing capsule. There may be a slight reduction in the peak pressure with which the drug is expelled, and various modifications to the shock absorbing component are possible to achieve a desired combination of the initial pressure profile and the pressure profile during the actual injection cycle.

For example, the degree of interference between the inner surface of the cylinder 150 and the ram may be altered to vary the reduction in initial pressure. For example, for a ram diameter of 4.0 mm, an inner diameter of the cylinder may typically be 3.77 mm, or it may be reduced to 3.6 mm to introduce greater frictional resistance. A typical tolerance may be 0.03 mm.

Figure 3:
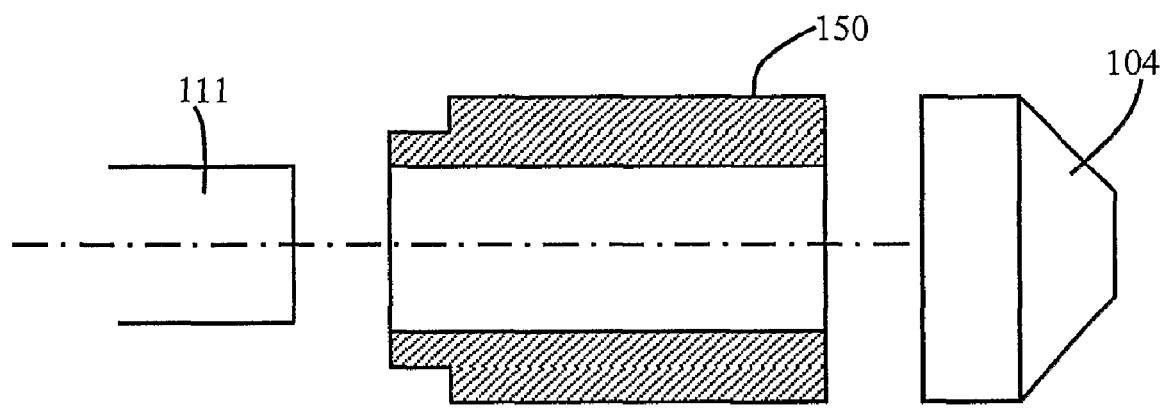
FIG. 3 shows a second example of shock absorbing component of the invention.

The design of shock absorbing component above has a closed end so that a sealed chamber is defined by the shock absorbing component in combination with the ram 111. However, the frictional interference alone may be sufficient. FIG. 3 shows a shock absorbing component 150 which is open at both ends. The amount of frictional resistance and the length can then be chosen to achieve the desired pressure profile.

Figure 4:
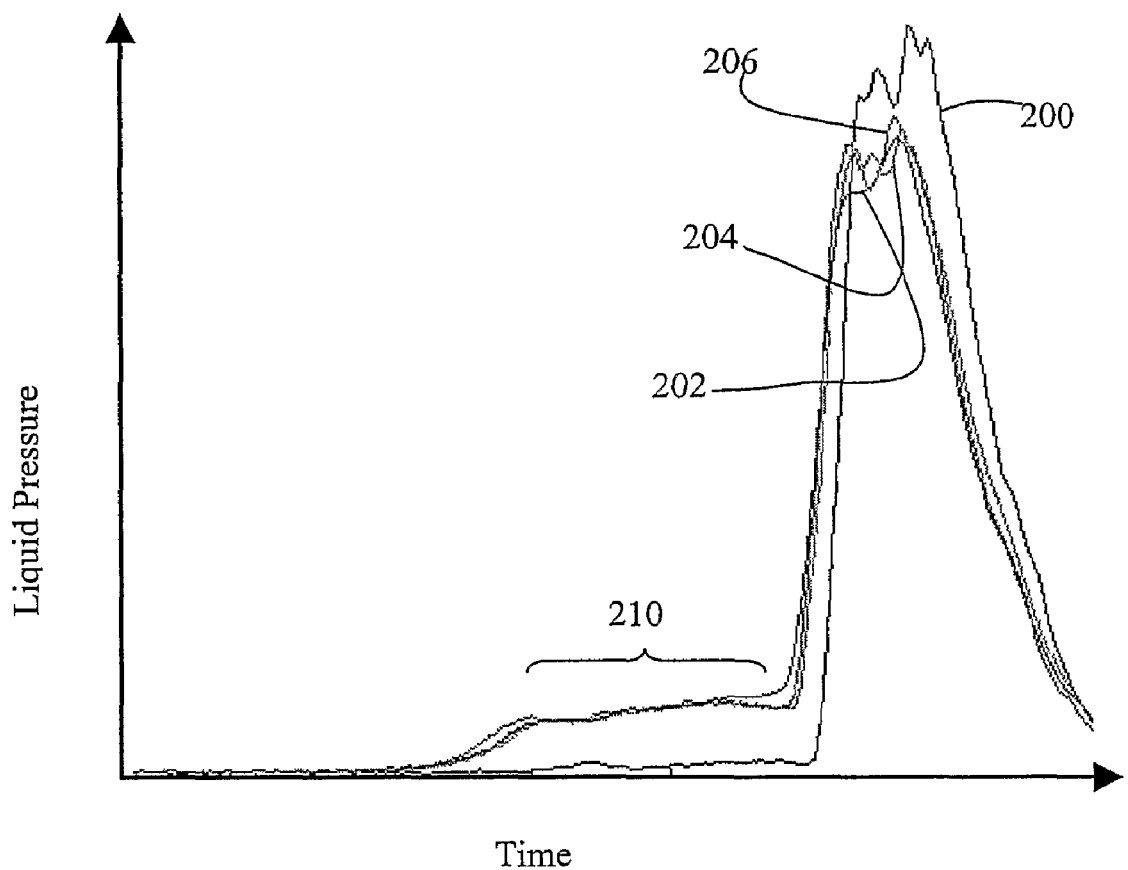
FIG. 4 shows pressure plots to illustrate the effect of the component of FIGS. 2 and 3.

FIG. 4 shows comparative pressure profiles for an injector with no shock absorbing component (plot 200), with the closed cylinder of FIG. 2 (plot 202) and two versions of the component of FIG. 3 of different lengths (plots 204—length 4.5 mm and 206—length 5 mm). As shown, thy presence of the shock absorbing component in each case provides the pressure region 210 which provides gradual bubble collapse, but the peak pressure surge at impact of the ram with the piston varies in the different designs.

It has been found (from studying fired devices) that there is significant deformation of the back of the piston 104 from the impact with the ram. Clearly, if such deformation can be reduced (which absorbs energy) this can provide an increased pressure peak at the point of impact of the ram with the piston (once the shock absorbing function has been completed).

Figure 5:
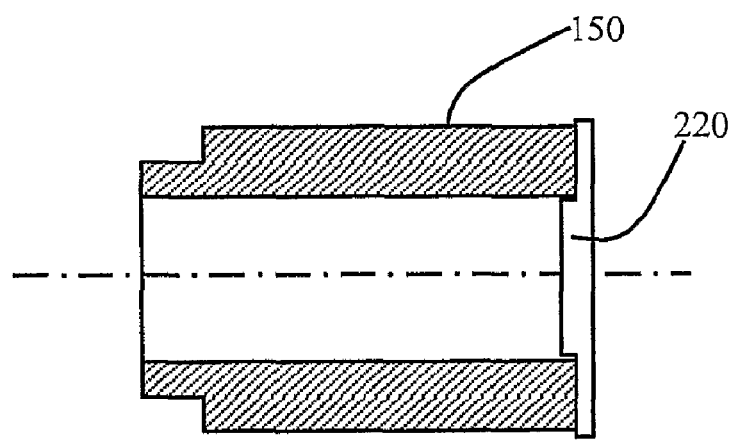
FIG. 5 shows a third example of shock absorbing component of the invention.

FIG. 5 shows a modification in which a metal end cap 220 is placed over the opening on the piston side of the shock absorber component. This is found to increase the peak pressure at the point in time when contact is made between the ram and the end cap. However, this increase in peak pressure is accompanied by a narrowing of the pressure peak, which may not be desirable.

Figure 6:
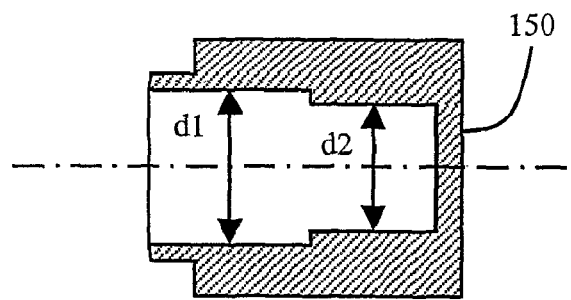
FIG. 6 shows a fourth example of shock absorbing component of the invention.

A further modification combines different degrees of frictional resistance within cylindrical bore. FIG. 6 shows a shock absorber having a closed end (as in FIG. 2) and in which two different internal diameters d1 and d2 are provided. The component is initially provided with a bore of diameter d2, and an additional counterboring step provides the increased internal diameter of d1 to a desired depth. Taking the example of the 4.0 mm diameter ram, d1 can equal 3.77 mm and d2 can equal 3.6 mm. The depth of the counterbore will of course influence the pressure profile characteristics. It will be seen that the height of the step between internal bore diameters is exaggerated in FIG. 6.

Figure 7:
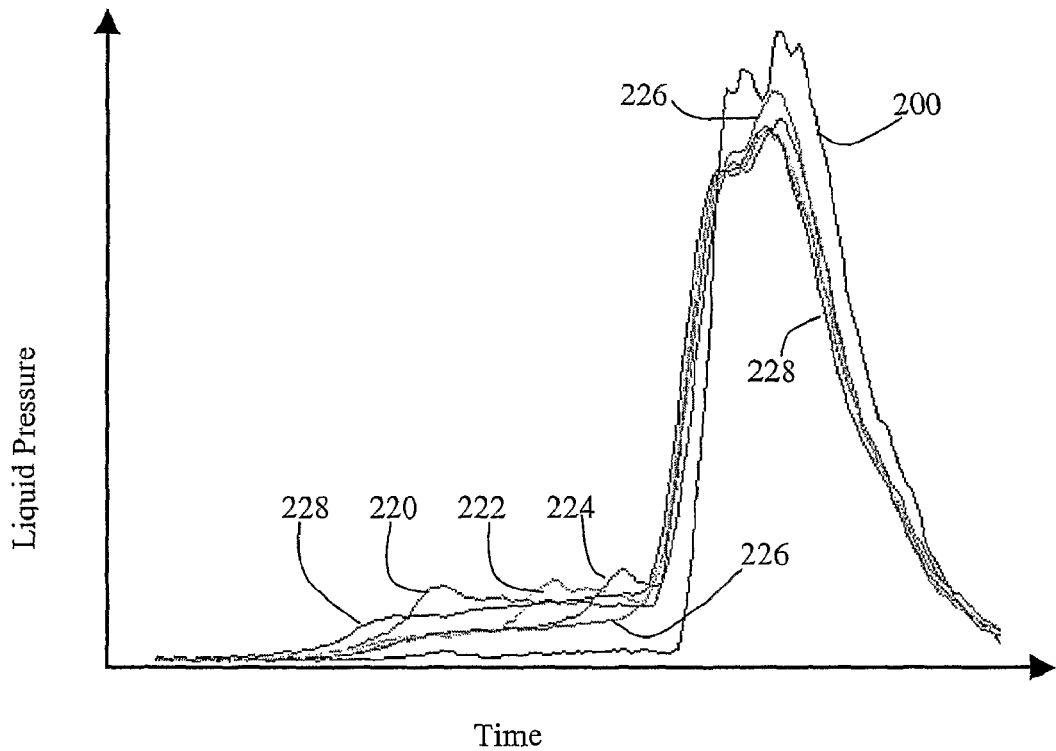
FIG. 7 shows pressure plots to illustrate the effect of the component of FIG. 6.

FIG. 7 shows comparative pressure profiles for an injector with no shock absorbing component (plot 200), and with counterbores to different depths (plots 220,222,224,226 show increasing depths of counterbore) as well as with no counterbore (namely an internal diameter of 3.6 mm for the full depth-plot 228).

Adding a counterbore to the open end of the component reduces the amount of friction and creates a short term pressure rise in the initial part of the liquid pressure profile as the ram rides over the shoulder between the different bore diameters. The deeper the counterbore, the nearer this pressure rise is to the main peak. This measure can thus be used to increase the peak pressure, and indeed in plot 226, the depth of the shoulder is such that the main pressure peak is increased.

Figure 8:
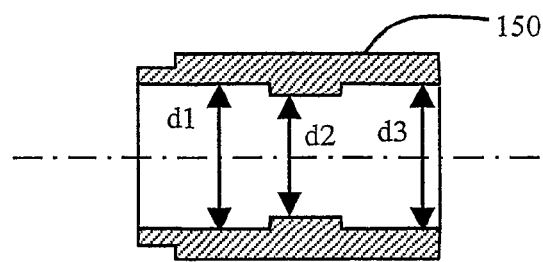
FIG. 8 shows a fifth example of shock absorbing component of the invention.

FIG. 8 shows a shock absorber open at both ends and in which three different internal diameters d1, d2 and d3 are provided. The component is initially provided with a bore of diameter d2, and an additional counterboring step provides the increased internal diameter of d1 to a desired depth from the ram side of the component and an additional counterboring step provides the increased internal diameter of d3 to a desired depth from the piston side of the component. As in FIG. 6, d1 can equal 3.77 mm and d2 can equal 3.6 mm for a ram diameter of 4.0 mm. The depths and diameters of the counterbores from both ends will influence the pressure profile characteristics.

Figure 9:
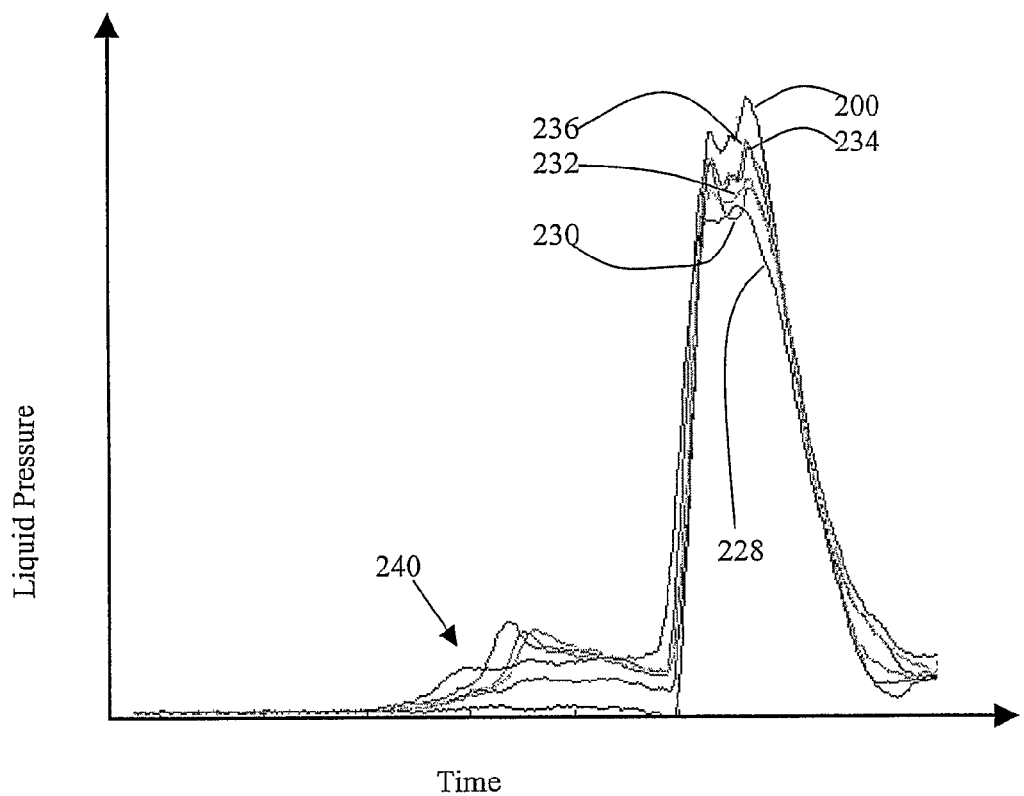
FIG. 9 shows pressure plots to illustrate the effect of the component of FIG. 8.

FIG. 9 shows comparative pressure profiles for an injector with no shock absorbing component (plot 200), for a component with no counterbore (namely an internal diameter of 3.6 mm for the full depth-plot 228 as in FIG. 7), and for components which differ only in the diameter of the piston side bore (plots 230,232,234,236 are for successively increasing values of d3). The plot closest to the original plot with no shock absorber is plot 236, and this is for a design in which the piston side counterbore is larger in diameter than the ram. This section of the shock absorber thus provides no additional resistance to the movement of the ram towards the piston, but does ensure that the low pressure in the drug is maintained for a suitable time period to enable slow bubble collapse. The plot 236 is for a component with d1=3.77 mm, d2=3.6 mm, d3=4.05 mm.

Designs with a rib as shown in FIG. 8 are found to provide the best combination of pressure profiles. The counterbore on the ram side of the component provides a step increase in pressure (shown as 240 in FIG. 9) which then drops, but a low pressure is maintained for gradual bubble collapse. The counterbore on the piston side reduces the amount of friction, thereby reducing the loss of peak pressure resulting from the presence of the shock absorbing component.

To anyone skilled in the art, it is clear that there are many methods of causing a gradual increase in pressure in a fluid constrained by a piston. Any component which reduces the initial pressure surge can be used, and there are many compressible elements which may be appropriate for this purpose. Whilst the invention has been shown as an improvement to one specific known design of needleless injector, the invention can be applied to many different designs, and one example only has been given above. In particular, there are many different ways of releasing stored energy to apply a force to the ram, other than the gas spring shown in the specific example.

The shock absorbing component may comprise part of the piston or the ram, or as in the example above it may effectively be defined by the interaction of these two components. The shock absorbing could also be applied to the output of the source of energy for driving the ram. The invention essentially provides any means for controlling the speed of bubble collapse within the liquid.

In another example, the internal opening of the cylindrical shock absorbing component can be greater in diameter than the diameter of the ram, and the ram can be coupled to the inner wall of the shock absorbing component through a grease which allows transfer of force, such as grease made by the company Kilopoise.

In the example above, the component is machined, and there are step changes in the internal diameter using counterboring techniques. There may instead be tapered changes to the internal diameter—for example the diameter of the opening in the cylinder may increase or decrease along the length of the component, or else a central rib may be defined, but with a taper to the larger opening size at the ends. This is of course more easily implemented for a moulded component.

Instead of the ram sliding through the shock absorbing component, it may push against it, for example it may be a rubber coupling member.

The term "shock absorbing means" has been used for the component of the invention, as it provides an initial lower pressure time period within the liquid before the main transfer of force from the ram to the piston. This is achieved by using some of the force (shock) from the ram. It could equally be described as means for providing an initial time period of relatively low pressure within the liquid before the main transfer of force from the ram to the piston. The term "shock absorbing means" is intended to cover all of these possibilities, including the implementation of the shock absorption by modification to the energy source (e.g. compressed gas source).

The invention claimed is:

1. A method of delivering liquid from a needleless injector syringe which comprises a piston housed within a syringe body and a ram for driving the piston thereby causing liquid to be driven out of the syringe, the method comprising:
   applying an initial force to the ram to initiate delivery of the liquid and collapse of a bubble in the liquid;
   during a first stage of the delivery, applying a reduced force to the piston thereby causing the bubble to collapse in a slow, controlled manner; and
   during a subsequent stage of the delivery, transferring substantially the full energy of the ram to the piston.

2. The method of claim 1, wherein when the reduced force is applied during the first stage by movement of the ram towards the piston causing compression of a closed volume of gas.

3. A method of preventing a collapsing bubble in a liquid formulation from causing a needle free injector capsule to break, comprising the step of causing the bubble to collapse in a slower, controlled manner immediately prior to the normal injection cycle.

4. The method of claim 3, wherein the step of causing the bubble to collapse in a slower, controlled manner comprises placing an additional component between the ram and the piston which causes an initial transfer of force from the ram to the piston which force is substantially smaller than the subsequent impact force between the ram and the piston.

5. The method of claim 4, wherein the initial transfer of force is caused by friction between the ram and the component which causes a force to be applied to the piston.

6. The method of claim 5, wherein the component is connected to an element chosen from the ram and the piston.

7. The method of claim 5, wherein the force applied to the piston causes the piston to move forward.

8. The method of claim 7, wherein the piston moving forward causes formulation pressure to increase to from 1 to 6 Mpa.

9. The method of claim 6, wherein the component comprises a cylinder, in which an end of the ram is slidably received.

10. The method of claim 9, wherein the cylinder forms part of the piston.

11. The method of claim 9, wherein the cylinder is closed at one end, the closed end lying adjacent the piston.

12. The method of claim 9, wherein the cylinder is open at both ends.

13. The method of claim 12, wherein the internal opening of the cylinder has a constant internal diameter.

14. The method of claim 13, wherein the bubble present within the liquid collapses to about 1/20 or less of an original size.

15. The method of claim 14, wherein the increase in pressure occurs within 200 μs.

16. A method of delivering liquid from a needleless injector syringe which comprises a piston housed within a syringe body and a ram for driving the piston thereby causing liquid to be driven out of the syringe, the method comprising:
   during a first stage of the delivery, applying a reduced force to the piston, thereby moving the piston forward slightly; and
   during a subsequent stage of the delivery, transferring substantially the full energy of the ram to the piston.

17. A method of reducing the propensity for a shock wave created from the rapid collapse of a gas bubble to break an injector syringe which comprises a piston housed within a syringe body and a ram for driving the piston thereby causing liquid to be driven out of the syringe, the method comprising:

applying an initial force to the ram, during a first stage of the delivery, applying a reduced force to the piston thereby causing the bubble to collapse in a slow, controlled manner; and during a subsequent stage of the delivery, transferring substantially the full energy of the ram to the piston.

18. A method of delivering a liquid formulation from a needle-free injector syringe, comprising a piston housed within a syringe body, a ram for driving the piston and a container for holding the liquid formulation, the method comprising:

applying a force profile to the ram, which force profile comprises a first stage followed by a second stage, wherein;

during the first stage of the force profile at least a portion of force applied to the ram is absorbed whereby a reduced force is applied to the piston; and during the second stage of the force profile substantially greater force as compared to the reduced force, is applied from the ram to the piston.

19. The method as claimed in claim 18, wherein a component is positioned between the ram and the piston.

20. The method as claimed in claim 19, wherein the component is a cylinder.

21. The method as claimed in claim 20, wherein cylinder comprised an internal opening that comprises three internal diameters, a third internal diameter at an end of the cylinder for cooperation with the piston, the third internal diameter being greater than the second internal diameter.

22. The method as claimed in claim 21, wherein the third internal diameter is equal to or greater than the diameter of the ram.

23. The method as claimed in claim 20, wherein the cylinder has a length of between 1 mm and 5 mm.

24. The method as claimed in claim 20, wherein the ram is slidably received in the cylinder with a fluid tight fit.

25. The method as claimed in claim 19, wherein the component is a shock absorbing means.

26. The method of claim 25, wherein the shock absorbing means comprises a compressible member.

27. The method of claim 17, wherein the force profile is provided by a source of pressurized fluid.

* * * * *